United States Patent [19]
Clement

[11] Patent Number: 5,892,233
[45] Date of Patent: Apr. 6, 1999

[54] STETHOSCOPE STERILIZER

[76] Inventor: Richard T. Clement, P.O. Box 80—3 Rue Kennedy Marigot, St. Martin 97051, France

[21] Appl. No.: 592,568

[22] Filed: Jan. 26, 1996

[51] Int. Cl.[6] .................................................... A61B 7/02
[52] U.S. Cl. ................................ 250/455.11; 250/504 R; 181/131
[58] Field of Search ......................... 250/455.11, 454.11, 250/493.1, 504 R; 422/24, 300; 181/131

[56] References Cited

U.S. PATENT DOCUMENTS

| | | | |
|---|---|---|---|
| 4,461,368 | 7/1984 | Plourde | 181/131 |
| 5,027,825 | 7/1991 | Phelps, Sr. et al. | 128/715 |
| 5,466,897 | 11/1995 | Ross et al. | 181/131 |
| 5,641,464 | 6/1997 | Briggs, III et al. | 422/300 |

*Primary Examiner*—Kiet T. Nguyen
*Attorney, Agent, or Firm*—John R. Lansdowne

[57] ABSTRACT

A device which is designed to simultaneously store and sterilize the head of a stethoscope within the pocket of a user during periods of non-usage. The small sterilizer is a box-shaped unit constructed of glass and plastic which fits into a shirt or jacket pocket, and which has a U-shaped lip which leads into an opening for receiving the head of the stethoscope. Beneath the lip is a switch that operates on contact with the stethoscope head to activate the unit, and the unit is powered by a small pen light batteries. An ultraviolet light is located proximate the U-shaped lip and delivers ultraviolet light rays through a circular transparent window aligned with the stethoscope head, and a clip on the back of the unit enables it to be easily attached to a user's pocket.

20 Claims, 3 Drawing Sheets

STETHOSCOPE STERILIZER

BACKGROUND OF THE INVENTION

1. Field of the Invention

The present invention pertains to ultraviolet light sterilizers, and more particularly pertains to a sterilizer which is particularly adapted for use with a stethoscope.

2. Description of the Prior Art

The use of ultraviolet light sterilizers is well known in the prior art. This is evidenced by the granting of a number of patents relating to various functional and structural aspects of such sterilizers. Examples of patented ultraviolet light sterilizers are to be found in U.S. Pat. No. 5,326,542 which issued to Sizer et al. on Jul. 5, 1994; U.S. Pat. No. 5,185,532 which issued to Zabsky et al. on Feb. 9, 1993; U.S. Pat. No. 4,906,851 which issued to Beasley et al. on Mar. 6, 1990; and U.S. Pat. No. 5,008,933 which issued to Kao et al. on Apr. 16, 1991.

While each of these prior art patents disclose ultraviolet light sterilizers which fulfill their respective particular objectives and requirements, and are most likely quite functional for their intended purposes, it will be noticed that none of them disclose sterilizers which are particularly adapted for use with stethoscopes and which are portable to the extent that they can be carried in the pocket of a user. As such, there apparently still exists the need for ultraviolet light sterilizers which would be designed for use with stethoscopes, and in this respect, the present invention substantially fulfills this need.

SUMMARY OF THE INVENTION

In view of the foregoing disadvantages inherent in the known types of stethoscope sterilizers now present in the prior art, the present invention provides a new stethoscope sterilizer having advantages and improvements which are patentably distinct over similar devices and methods which may already be patented or commercially available. As such, the general purpose of the present invention, which will be described subsequently in greater detail, is to provide a stethoscope sterilizer and method which has many of the advantages of the stethoscope sterilizers mentioned heretofore while being operable to overcome problems not presently addressed by the prior art.

To attain this, the present invention generally comprises a device which is designed to simultaneously store and sterilize the head of a stethoscope within the pocket of a user during periods of non- usage. The small sterilizer is a box-shaped unit constructed of glass and plastic which fits into a shirt or jacket pocket, and which has a U-shaped lip which leads into an opening for receiving the head of the stethoscope. Beneath the lip is a switch that operates on contact with the stethoscope head to activate the unit, and the unit is powered by a small pen light batteries. An ultraviolet light is located proximate the U-shaped lip and delivers ultraviolet light rays through a circular transparent window aligned with the stethoscope head, and a clip on the back of the unit enables it to be easily attached to a user's pocket.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new stethoscope sterilizer and method which has many of the advantages of the stethoscope sterilizers mentioned heretofore and many novel features that result in a stethoscope sterilizer which solves problems not presently addressed in the prior art.

It is another object of the present invention to provide a new stethoscope sterilizer which may be easily and efficiently manufactured and marketed.

It is a further object of the present invention to provide a new stethoscope sterilizer which is of a durable and reliable construction.

An even further object of the present invention is to provide a new stethoscope sterilizer which is susceptible of a low cost of manufacture with regard to both materials and labor, and which accordingly is then susceptible of low prices of sale to the consuming public, thereby making such stethoscope sterilizer economically available to the buying public.

Still yet another object of the present invention is to provide a new stethoscope sterilizer which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF PREFERRED EMBODIMENTS

Figure 1:
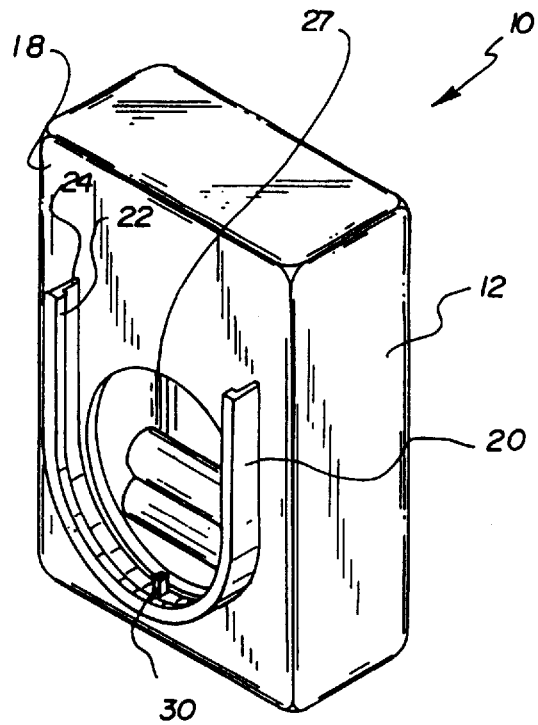
FIG. 1 is a perspective view of the stethoscope sterilizer comprising the present invention.
Figure 2:
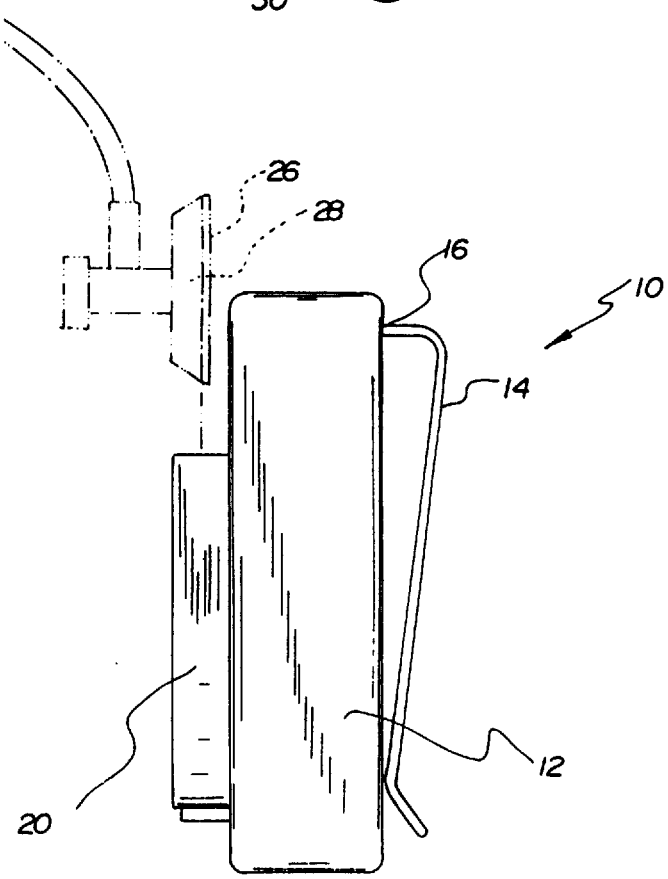
FIG. 2 is a side elevation view of the invention.
Figure 3:
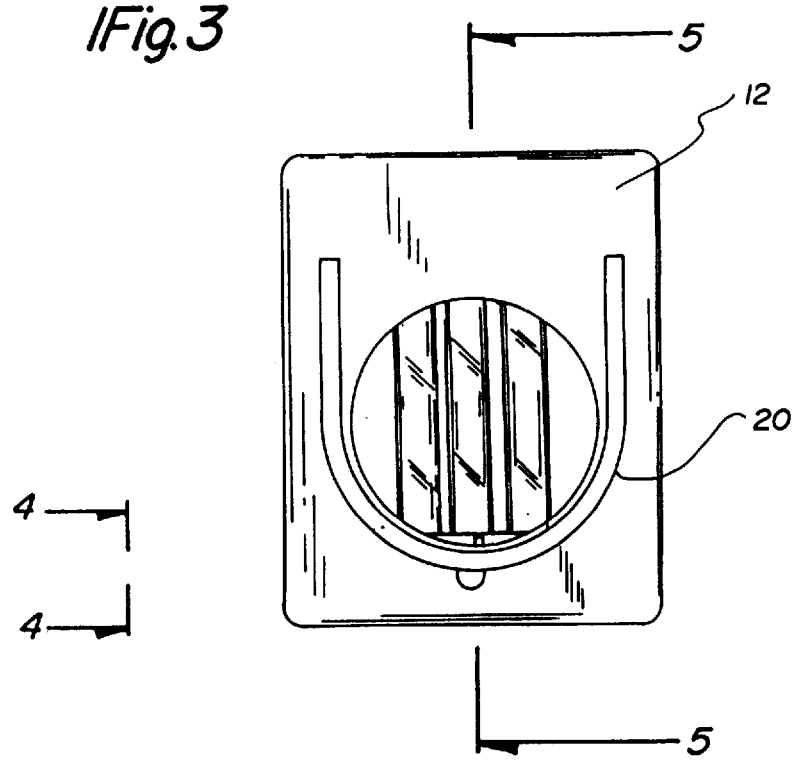
FIG. 3 is a front elevation view of the invention.

With reference now to the drawings, and in particular to FIGS. 1–6 thereof, a new stethoscope sterilizer embodying the principles and concepts of the present invention and generally designated by the reference numeral 10 will be described.

More specifically, it will be noted that the stethoscope sterilizer 10 includes a box-shaped housing 12 which is constructed of a material such as glass or clear plastic and which is of a size which will facilitate its fitting into a shirt or jacket pocket of a user. A pocket clip 14 on a rear surface 16 of the sterilizer 12 is of a conventional design and facilitates the removable attachment of the sterilizer to an outside pocket area or on a belt of a user.

A front face 18 of the sterilizer housing 12 is provided with a U-shaped support bracket 20 having an outer continuous lip 22 positioned thereabout so as to define a continuous groove 24 interiorly of the bracket and lying in juxtaposition with the front face 18. An outer edge 26 of a stethoscope head 28 is slidably positionable within the groove 24, and when totally positioned therein, the edge 26 will abut against a push button switch 30 mounted on a bottom portion of the bracket 20.

Figure 4:
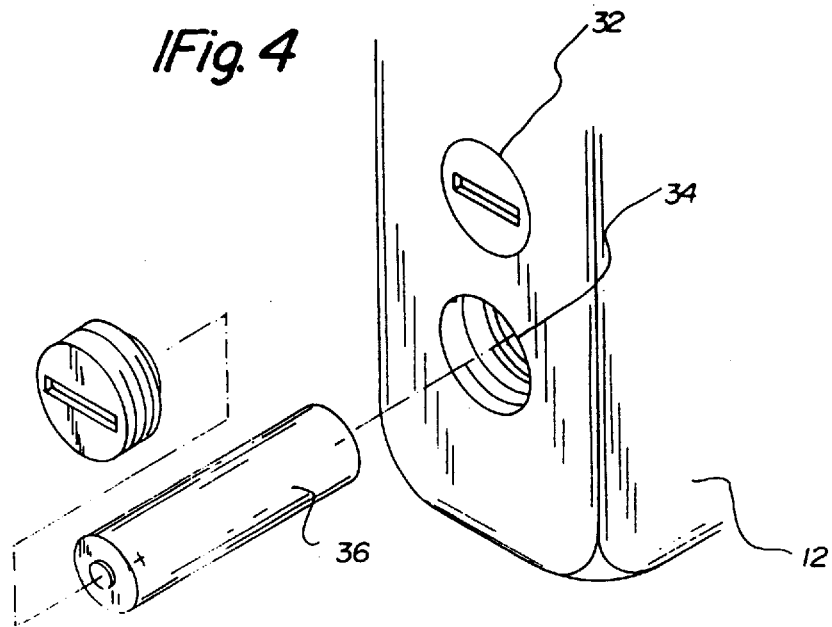
FIG. 4 is a cross-sectional view of the invention as viewed along the line 4—4 in FIG. 3.
Figure 5:
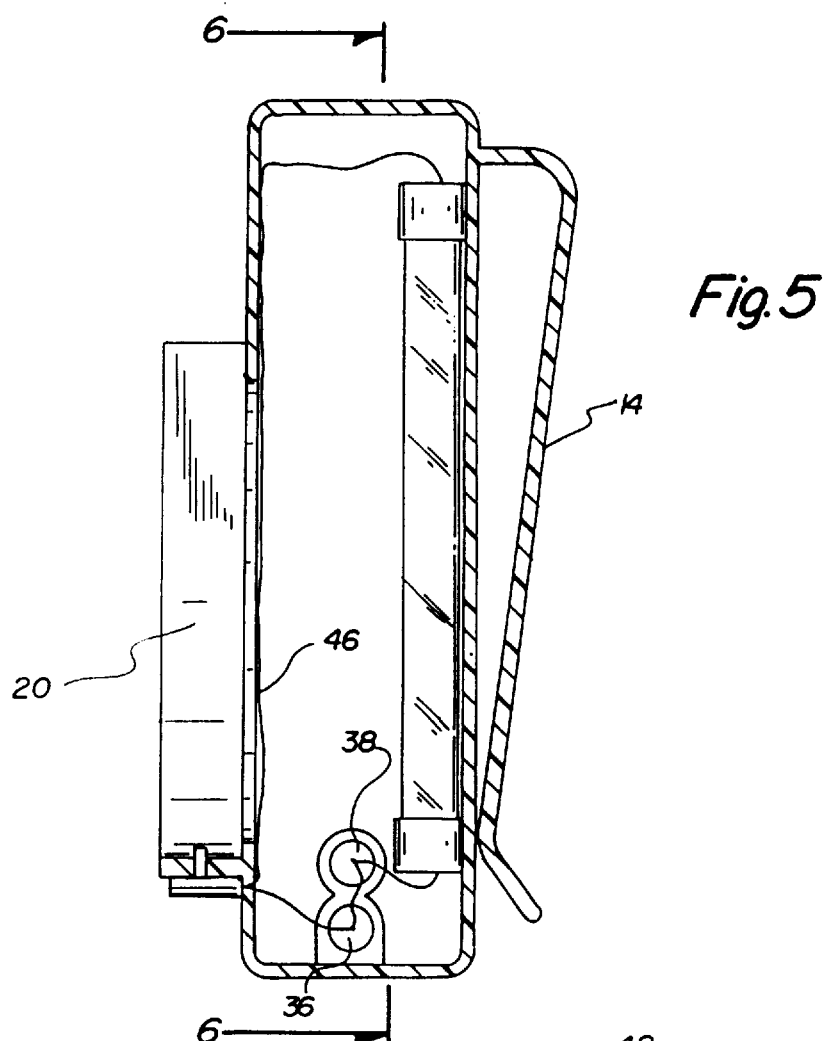
FIG. 5 is a cross-sectional view of the invention as viewed along the line 5—5 in FIG. 3.
Figure 6:
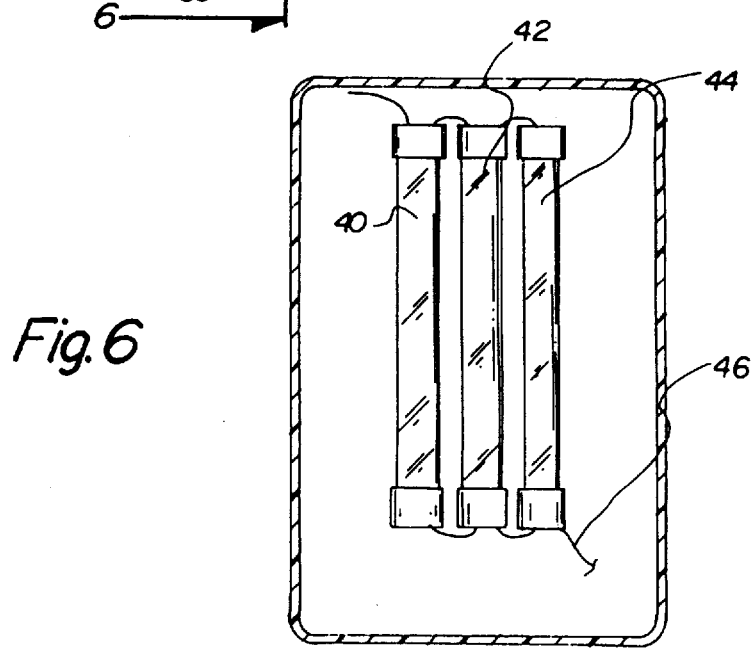
FIG. 6 is a cross-sectional view of the invention as viewed along the line 6—6 in FIG. 5.

A pair of battery receiving openings 32, 34, as shown in FIG. 4, are designed to receive a pair of pen light batteries 36, 38, and these batteries provide electrical power to several small ultraviolet lamps 40, 42, 44. While three such ultraviolet lamps 40, 42, 44 are shown in the preferred embodiment 10 of the invention, it is to be understood that any number, shape and size of such lamps are within the intent and purview of the present invention, and are intended to be encompassed by the claims appended hereto.

A circular opening 27 is conformingly positioned within a bottom circular part of the U-shaped bracket 20, and the opening effectively defines a window through which ultraviolet light rays may be directed from the lamps 40,42,44 so as to impinge in a sterilizing manner upon the stethoscope head 28 retained within the bracket. The opening 27 may be uncovered, or in the alternative, it may be covered with a layer of protective light transmissive material such as a clear transparent plastic or glass. The lamps 40, 42, 44 may be mounted anywhere inside of the housing 12 and by any conventional means, to include brackets, adhesives, etc.

As shown, the push button switch 30 is mounted in a circuit defined by a continuous electrical conductor 46, and when a stethoscope head 28 abuts thereagainst so as to be in a stored non-use position, the switch is closed to thereby close the circuit and activate the lamps 40, 42, 44. As such, the sterilizing effect continues during the complete storage time of the stethoscope head within the unit, and when the head of the stethoscope is removed for use, it is clean and sterilized.

Doctors, nurses, and other medical office assistants usually do not have an effective way to clean stethoscope heads between visits with patients without damaging the head itself. Therefore, this leaves each and every patient at risk of coming into contact with a contagious disease transmitted from a prior patient. This inexpensive sterilizer 10 should reduce the risks of contagion on the stethoscope, making routine use of this instrument much safer.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A stethoscope sterilizer comprising:

a housing means;

power supply means positioned within said housing means;

at least one ultraviolet lamp mounted in said housing means;

stethoscope head receiving and holding means; and switch means for activating said at least one ultraviolet lamp.

2. The stethoscope sterilizer as described in claim 1 and further wherein said stethoscope receiving and holding means comprises a U-shaped bracket mounted on said housing means.

3. The stethoscope sterilizer as described in claim 2, wherein said bracket is provided with a groove interiorly thereof, said groove being receivable of an edge of a stethoscope head so as to retain said stethoscope head within said bracket.

4. The stethoscope sterilizer as described in claim 3, wherein said U-shaped bracket is mounted against a transparent face of said housing means.

5. The stethoscope sterilizer as described in claim 4, wherein said switch means is mounted in a bottom end of said U-shaped bracket, said switch means being normally open and being closed as a result of an insertion of said stethoscope head into said U-shaped bracket.

6. The stethoscope sterilizer as described in claim 5, wherein said power supply means includes at least one battery mounted within said housing means.

7. The stethoscope sterilizer as described in claim 6, wherein said housing means includes an opening positioned proximate said stethoscope head when said head is positioned within said U-shaped bracket.

8. The stethoscope sterilizer as described in claim 7, wherein said opening is covered by a transparent material to thereby define said transparent face.

9. The stethoscope sterilizer as described in claim 7, and further including a clip for facilitating an attachment of said housing means on an article of clothing worn by a user.

10. The stethoscope sterilizer as described in claim 9, wherein said housing is of a size designed to fit within a pocket of said article of clothing worn by said user.

11. A stethoscope sterilizer comprising:

a housing means;

power supply means positioned within said housing means;

at least one ultraviolet lamp mounted in said housing means;

stethoscope head receiving and holding means attached to said housing means;

switch means connected to said power supply means for activating said at least one ultraviolet lamp; and means for transmitting light from said at least one ultraviolet lamp to illuminate said stethoscope head receiving and holding means.

12. The stethoscope sterilizer as described in claim 11, wherein said stethoscope receiving and holding means comprises a U-shaped bracket mounted on said housing means.

13. The stethoscope sterilizer as described in claim 12, wherein said bracket is provided with a groove interiorly thereof, said groove being receivable of an edge of a stethoscope head so as to retain said stethoscope head within said bracket.

14. The stethoscope sterilizer as described in claim 13, wherein said switch means is mounted in a bottom end of said U-shaped bracket, said switch means being normally open and being closed as a result of an insertion of said stethoscope head into said U-shaped bracket.

15. The stethoscope sterilizer as described in claim 13, wherein said housing means includes an opening positioned proximate said stethoscope head when said head is positioned within said U-shaped bracket.

16. The stethoscope sterilizer as described in claim 15, wherein said opening is covered by a transparent material to thereby define said transparent face.

17. The stethoscope sterilizer as described in claim 12 wherein said U-shaped bracket is mounted against a transparent face of said housing means.

18. The stethoscope sterilizer as described in claim 11, wherein said power supply means includes at least one battery mounted within said housing means.

19. The stethoscope sterilizer as described in claim 11 and further comprising a clip for facilitating an attachment of said housing means onto an article of clothing worn by a user.

20. The stethoscope sterilizer as described in claim 11, wherein said housing is of a size designed to fit within a pocket of an article of clothing worn by a user.

* * * * *